United States Patent
Werneth

(10) Patent No.: US 8,647,336 B2
(45) Date of Patent: Feb. 11, 2014

(54) CRYOGENIC MEDICAL DEVICE WITH THERMAL GUARD AND METHOD

(75) Inventor: Randell L. Werneth, San Diego, CA (US)

(73) Assignee: Medtronic Ablation Frontiers LLC, Minneapolis MN ( * ) Notice: Subject to any disclaimer, the term of this patent is extended or adjusted under 35 U.S.C. 154(b) by 816 days.

(21) Appl. No.: 12/816,479

(22) Filed: Jun. 16, 2010

(65) Prior Publication Data

US 2011/0313410 A1 Dec. 22, 2011

(51) Int. Cl.
*A61B 18/02* (2006.01)

(52) U.S. Cl.
USPC .............................................. 606/23; 606/20

(58) Field of Classification Search
USPC ....................................... 606/20–26
See application file for complete search history.

(56) References Cited

U.S. PATENT DOCUMENTS

| | | | | |
|---|---|---|---|---|
| 3,794,039 | A * | 2/1974 | Kollner et al. | 606/22 |
| 5,314,423 | A * | 5/1994 | Seney | 606/20 |
| 5,720,743 | A * | 2/1998 | Bischof et al. | 606/1 |
| 5,868,735 | A * | 2/1999 | Lafontaine | 606/21 |
| 5,902,251 | A | 5/1999 | Vanhooydonk | |
| 5,989,246 | A | 11/1999 | Kaufman et al. | |
| 6,159,207 | A | 12/2000 | Yoon | |
| 6,394,949 | B1 | 5/2002 | Crowley et al. | |
| 6,547,784 | B1 * | 4/2003 | Thompson et al. | 606/21 |
| 6,629,972 | B2 * | 10/2003 | Lehmann et al. | 606/22 |
| 2002/0087156 | A1 | 7/2002 | Maguire et al. | |
| 2003/0036752 | A1 * | 2/2003 | Joye et al. | 606/21 |
| 2003/0050631 | A1 * | 3/2003 | Mody et al. | 606/15 |
| 2004/0199154 | A1 * | 10/2004 | Nahon et al. | 606/21 |
| 2006/0079867 | A1 | 4/2006 | Berzak et al. | |
| 2008/0033414 | A1 * | 2/2008 | Levin et al. | 606/21 |
| 2008/0294154 | A1 * | 11/2008 | Ibrahim et al. | 606/13 |
| 2010/0100087 | A1 | 4/2010 | Mazzone et al. | |

FOREIGN PATENT DOCUMENTS

| | | |
|---|---|---|
| EP | 1384445 A1 | 1/2004 |
| WO | 9905979 A1 | 2/1999 |
| WO | 0207628 A2 | 1/2002 |

* cited by examiner

*Primary Examiner* — Michael Peffley
(74) *Attorney, Agent, or Firm* — Christopher & Weisberg, P.A.

(57) ABSTRACT

A medical device, system and method are provided for thermal medical treatment. A medical device for cryogenic treatment may include a tip and a thermal guard or shield. The tip may be at a distal end of a catheter shaft, having a distal surface and lateral surfaces. The thermal guard may be coupled to the catheter proximal of the distal tip, surrounding the longitudinal axis and exposing the distal surface, to resist heat transfer from body fluids to the lateral surfaces of the tip. An efficiency of heat transfer from selected tissue to be treated to the distal surface of the cryogenic tip is thereby increased.

14 Claims, 4 Drawing Sheets

CRYOGENIC MEDICAL DEVICE WITH THERMAL GUARD AND METHOD

CROSS-REFERENCE TO RELATED APPLICATION

N/A

STATEMENT REGARDING FEDERALLY SPONSORED RESEARCH OR DEVELOPMENT

N/A

FIELD OF THE INVENTION

The present invention relates to medical treatment systems and methods of use thereof.

BACKGROUND OF THE INVENTION

Medical procedures are available for treatment of a variety of cardiovascular maladies, such as for example cardiac arrhythmias, atrial fibrillation, and other irregularities in the transmission of electrical impulses through the heart. As an alternative to open-heart surgery, many medical procedures are performed using minimally invasive surgical techniques, where one or more slender implements are inserted through one or more small incisions into a patient's body. Such procedures may involve the use of catheters having multiple sensors, electrodes, cryogenic chambers, or other measurement and treatment components to treat the diseased area of the heart, vasculature, or other tissue. Catheter-based devices are desirable for various medical and surgical applications because they are relatively non-invasive and allow for precise treatment of localized discrete tissues that are otherwise inaccessible. Catheters may be easily inserted and navigated through the blood vessels and arteries, allowing non-invasive access to areas of the body with relatively little trauma. Typically, such minimally invasive and intravascular devices are routed through a femoral artery or other passageway into the heart under guided fluoroscopy or other imaging techniques.

One such example of a minimally-invasive treatment modality involves the treatment of cardiac arrhythmias or irregular heartbeats in which physicians employ specialized ablation catheters to gain access to interior regions of a patient's body. Such catheters may include an ablation tip or other ablating elements to create lesions or other anatomical effects that physiologically alter the ablated tissue without removal thereof, disrupting or blocking electrical pathways through the targeted tissue. In the treatment of cardiac arrhythmias, a specific area of cardiac tissue having aberrant electrically conductive pathways with erratic electrical impulses is typically initially localized. An ablation procedure may involve creating one or more lesions in order to electrically isolate tissue believed to be the source of an arrhythmia. During the course of such a procedure, a physician may diagnose aberrant tissue and cryogenically destroy it. Cryotreatment or cryogenic ablation entails creating cold temperatures at specific regions of the body or contacting tissue with cold treatment devices. In particular, cryoablation involves transferring heat from the targeted tissue to the cryogenic element, thus cooling and/or ablating the tissue.

Cryogenic treatments may involve fluids with low operating temperatures, or cryogens, with the use of catheter-based devices employing the flow of cryogenic working fluids to selectively freeze, or "cold-treat," targeted tissues within the body. A cryogenic device uses the energy transfer derived from thermodynamic changes occurring in the flow of a refrigerant through the device. This energy transfer is then utilized to create a net transfer of heat flow from the target tissue to the device, typically achieved by cooling a portion of the device to very low temperature through conductive and convective heat transfer between the refrigerant and target tissue. The quality and magnitude of heat transfer is regulated by device configuration and control of the refrigerant flow regime within the device. While cardiac arrhythmias present one example, such "cold energy" can be safely and effectively used to treat a host of medical conditions by creating endothermic heat transfer from a surgical tool relative to a region of tissue, so as to induce localized hypothermia of varying severity.

To provide shorter treatment durations and increased efficacy for the particular treatment provided, it is desirable to optimize the heat transfer between the specific tissue to be treated and the cryogenic element or device. In other words, heat transfer from any tissue other than that selected for treatment, such as blood or other body fluids in or passing through the vicinity of the cryogenic element for example, should be minimized or avoided. Such thermal exchange with tissues or fluids other than that targeted for treatment can reduce the thermal exchange with the targeted tissue and also require additional "cooling power" or refrigerant flow to the cryogenic device in order to complete the desired treatment. Accordingly, heat transfer with any thermal load other than the tissue to be treated should be reduced or prevented. It would be desirable to provide an apparatus and method of increasing the efficiency of heat transfer during cryogenic treatments between the tissue selected for treatment and the cryogenic element used to treat the tissue.

SUMMARY OF THE INVENTION

The present invention advantageously provides a medical device, system, and method for thermally treating a patient with increased heat transfer efficiency. In particular, a medical device is provided, including an elongate shaft having a proximal end and a distal end and a fluid path therethrough; a thermal treatment element at the distal end and in fluid communication with the fluid path; and a thermal guard coupled to the shaft and substantially surrounding the thermal treatment element. The thermal treatment element may include a chamber having a lateral surface and a distal surface, and the thermal guard substantially surrounds the lateral surface. The device may include a cryogenic fluid source in fluid communication with the fluid path, and the thermal guard can be removably coupled to the elongate shaft. An annular gap may be defined between the thermal guard and the thermal treatment element, and the thermal guard may define one or more pleats, have a substantially cylindrical shape, be substantially impervious to fluids, and/or include an inflatable element. The shaft may define a second fluid path in fluid communication with the inflatable element.

A cryogenic medical system is also provided, having a catheter having a distal tip defining a chamber with a lateral surface and a distal surface; a cryogenic fluid supply in fluid communication with the chamber; and a thermal guard coupled to the catheter at a position proximal of the distal tip, the thermal guard substantially surrounding the lateral surface and exposing the distal surface.

A method of cryogenic treatment is also provided, including positioning a distal surface of a catheter tip into contact with tissue to be treated; shielding lateral surfaces of the tip from contact with body fluids; circulating a coolant through a chamber inside the tip; and ablating the tissue with the distal surface. The tissue may include cardiac tissue, and the method may also include monitoring a temperature of the tip.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein.

DETAILED DESCRIPTION OF THE INVENTION

Figure 1:
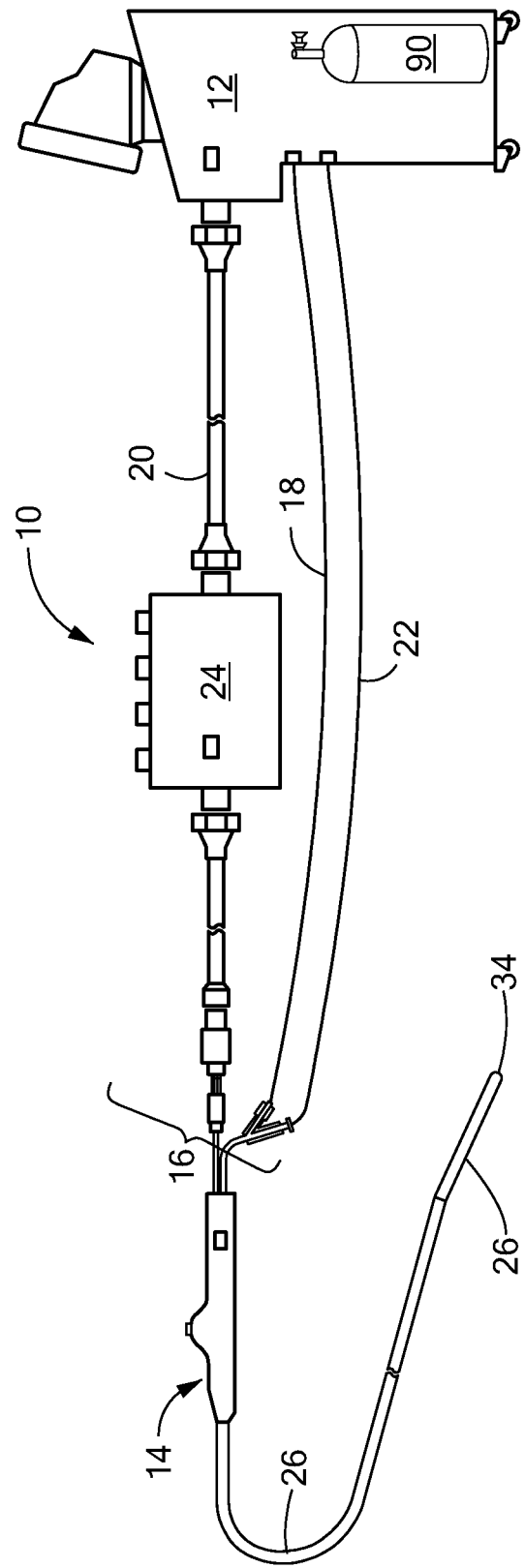
FIG. 1 is an illustration of an exemplary medical system constructed in accordance with the principles of the present invention.

The present invention provides medical devices, systems and methods of use thereof having features for increasing heat transfer efficiency for cryogenic medical treatments. Referring now to the drawings in which like reference designators refer to like elements, there is shown in FIG. 1 an exemplary embodiment of a medical system for treating tissue, such as cardiac tissue, designated generally as 10. Of note, the device components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein may be included in a variety of different combinations or configurations without departing from the scope and spirit of the invention.

As shown in FIG. 1, the system 10 generally includes a cooling unit or console 12 coupled to a medical device 14 through an umbilical system 16. The medical device 14 may be a medical probe, a catheter, a balloon-catheter, or any other devices deliverable or otherwise positionable through the vasculature and/or proximate to a tissue region selected for treatment. In particular, the medical device 14 may include a device operable to thermally treat a selected tissue site, including cardiac tissue. The medical system 10 may also include one or more sensors to monitor the operating parameters throughout the system, including for example, pressure, temperature, flow rates, volume, or the like in the console 12, the umbilical system 16, and/or the medical device 14.

Umbilical system 16 may include three separate umbilicals: a coaxial cable umbilical 18, an electrical umbilical 20 and a vacuum umbilical 22. Although separate umbilicals are shown, it is contemplated that one or more connections may be included in one or more umbilicals having one or more coaxial or otherwise integrally contained passages or conduits therethrough providing electrical and fluid communication between the medical device 14 and the console 12. If the user wishes to perform a radiofrequency ("RF") ablation procedure, radiofrequency energy can be provided to electrodes on the medical device 14 via electrical umbilical 20 to perform an RF ablation technique. In addition, electrical umbilical 20 can include an electrocardiograph ("ECG") box 24 to facilitate a connection from one or more electrodes on the medical device 14 to an ECG monitor (not shown). Coaxial umbilical 18 may include both a cooling injection umbilical and a vacuum umbilical that provide respective inlet and return paths for a refrigerant or coolant used to cool a tissue-treating section of the device 14. The vacuum umbilical 22 may provide a safety conduit allowing excess coolant or gas to escape from the device 14 if the pressure within the medical device 14 exceeds a predefined limit. The vacuum umbilical 22 can also be used to capture air through a leak of the outer vacuum system where it is outside the patient and as a lumen to ingress blood when inside the patient.

Figure 2:
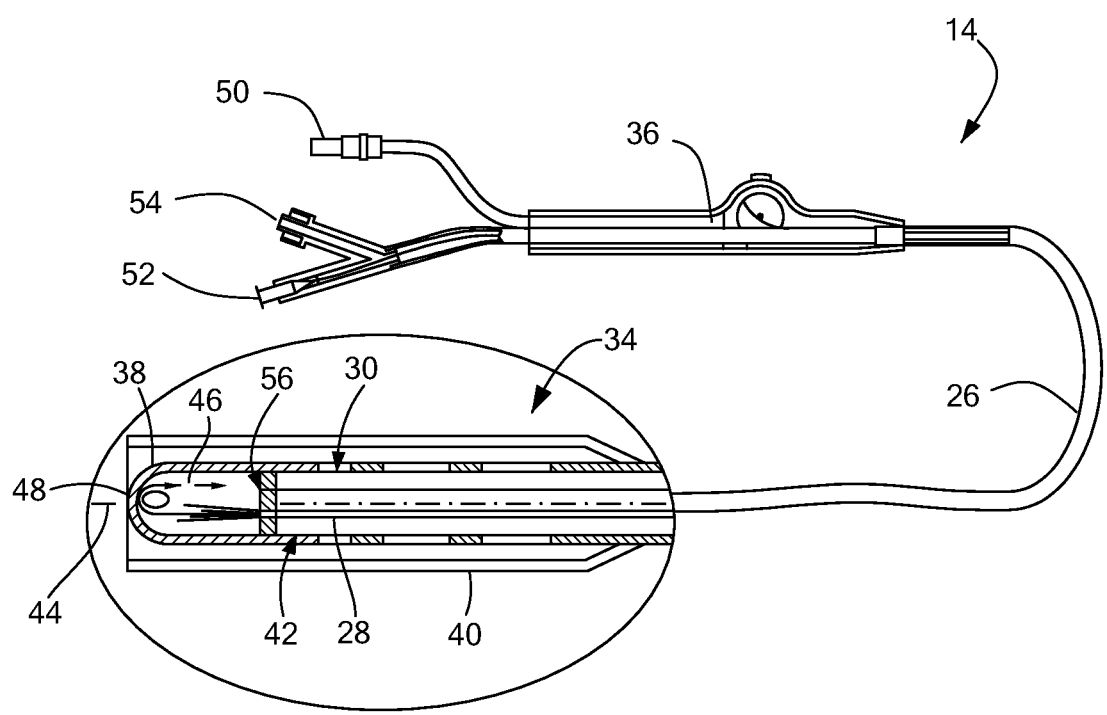
FIG. 2 is an illustration of an exemplary medical device constructed in accordance with the principles of the present invention.

Now referring to FIG. 2, the medical device 14 is shown in more detail. The medical device 10 may include an elongate body 26 which can navigate through a patient's vasculature or other body passages. The elongate body 26 may define a proximal portion and a distal portion, and may further include one or more lumens disposed within the elongate body 26 thereby providing mechanical, electrical, and/or fluid communication between the proximal portion of the elongate body 26 and the distal portion of the elongate body 26. For example, the elongate body 26 may include an injection lumen 28 and an exhaust lumen 30 defining a fluid flow path therethrough. In addition, the elongate body 26 may include a guidewire lumen disposed within and/or extending along at least a portion of the length of the elongate body 26 for over-the-wire applications.

The shaft body 26 of the medical device 14 defines a proximal end 32 and a distal end 34, a handle 36 affixed to the proximal end 32, and one or more treatment regions for energetic or other therapeutic interaction between the medical device 14 and a treatment site. A treatment region or element may provide, for example, radiofrequency energy, cryogenic therapy, or the like. The medical device may include a treatment region having a thermal treatment element disposed on the elongate catheter body 26 at or near its distal end 34 to provide any of the above-named energetic treatments.

As shown in FIG. 2, the thermal treatment element may be a cryogenic tip 38, as well as a shield, hood, or thermal guard 40 substantially surrounding lateral surfaces 42 of the cryogenic tip 38. The distal cryogenic tip 38 defines a longitudinal axis 44, an internal chamber 46, and a distal surface 48. The chamber 46 defined at the tip may be an elongated chamber several centimeters in length able to form an elongated or otherwise linear lesion when placed in contact with tissue such as the cardiac wall while also providing for the creation of "spot" lesions using the distal surface 48. Furthermore, the chamber wall may be very thin, or formed with a metal sleeve or cap to achieve high heat transfer rates. Examples of materials preferentially used to construct such a cryochamber are polymers, plastics, non-ferrous metals such as gold or copper, or a mixture thereof. The injection lumen 28 and the exhaust lumen 30 are in fluid communication with the internal chamber 46 defined by the cryogenic tip 38 to define a fluid flow path therethrough facilitating the delivery and/or circulation of a refrigerant or coolant, such as a cryogenic fluid.

Figure 3:
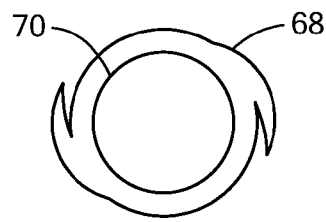
FIG. 3 is an illustration of another exemplary medical device constructed in accordance with the principles of the present invention.
Figure 4:
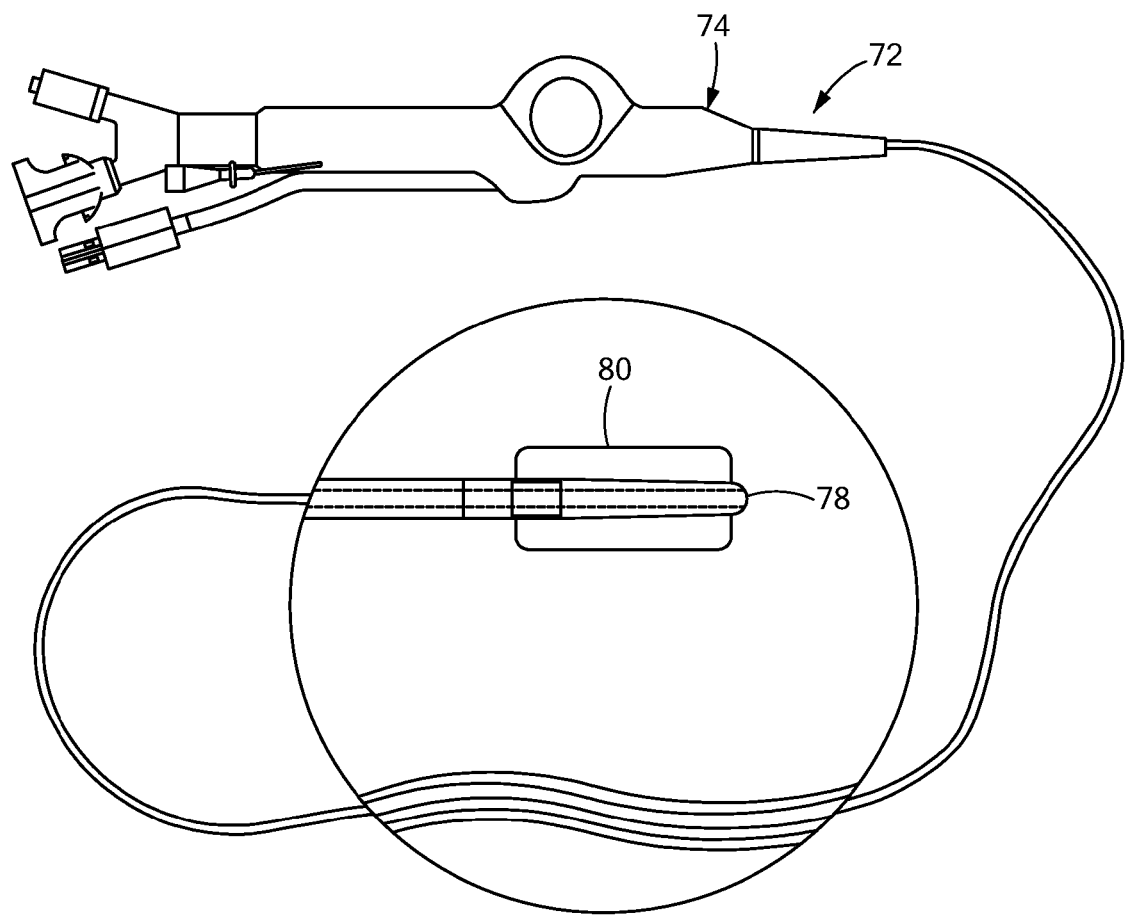
FIG. 4 is an illustration of yet another exemplary medical device constructed in accordance with the principles of the present invention.

The thermal guard 40 may be coupled to the catheter shaft 26 at a position proximal of the cryogenic tip 38 and coaxial with the longitudinal axis 44 to expose the distal surface 48 of the cryogenic tip 38. The thermal guard 40 may have various shapes, arrangements, and configurations. For example, the thermal guard 40 may include a cylindrical shape, creating an annular gap between an interior surface of the thermal guard 40 and the lateral surfaces 42 of the cryogenic tip 38. As shown in FIG. 3, a thermal guard 68 is shown in an initial configuration, which is pleated around the longitudinal axis of a cryogenic element 70. Such pleating enables the thermal guard 68 to be tightly wrapped around the cryogenic element 70 during advancement of the catheter to the desired site for treatment, then expanding slightly to form an annular gap around cryogenic element 70 for enhanced thermal shielding of the lateral sides of cryogenic element 70. Another thermal guard is illustrated in FIG. 4, showing a cryogenic catheter 72 having a handle 74, a flexible shaft 76, a cryogenic tip 78, and an expandable thermal guard 80. The thermal guard 80 may be an inflatable balloon or any other suitable expandable element, and provides thermal shielding of the lateral sides of the cryogenic tip 78. Expandable thermal guard 80 may take the form of a balloon that can be inflated and deflated by an independently operable inflation and/or exhaust lumens (not illustrated). The inflation media may include an insulating fluid having low thermal conductivity characteristics.

The thermal guard 40 may be permanently or removably coupled to the shaft body 26 and may be constructed from various materials providing thermal insulation, resilience, and/or flexibility, in addition to being substantially impervious to fluids. In use, when the cryogenic tip 38 is in an environment containing blood or other body fluids, the thermal guard 40 shields or otherwise insulates the lateral surfaces 42 of the cryogenic tip 38 from the body fluids near or flowing past the tissue to be treated. This shielding or insulation reduces or eliminates heat transfer between the surrounding body fluids and the cryogenic tip 38, resulting in the focused heat transfer between the targeted tissue to be treated to the cryogenic tip 38. Accordingly, the thermal guard 40 increases the efficiency of heat transfer during cryogenic treatments, which can reduce treatment duration as well as the amount of coolant or refrigerant needed to perform the desired treatment.

Referring again to FIG. 2, the handle 36 of the medical device 14 may be equipped with input ports for an electrical connector 50, a coolant injection tube connector 52, and a return tube connector 54. These connect via various internal junctions or tubes passing through the handle to provide these three functions to the distal tip of the catheter. The handle 36 may also include various control assemblies, such as for example steering actuators for manipulating steering elements such as pull wires to direct and steer portions of the shaft body 26, the cryogenic tip 38, and/or the thermal guard 40. The handle 36 may further include one or more switches, sensors, valves, as well as safety detection or shut down elements (not illustrated).

A thermocouple or other sensor 56 may be positioned on or within the distal end 34 to sense temperature, and a plurality of electrodes may be positioned near the distal end 34 for use in mapping and/or detecting cardiac signals. Other structures within the medical device 14 may include torque or steering wires, or other elements conventional in the art for navigation of the catheter past branch points in vessels, and for urging the tip 38 into contact with a wall once its position is confirmed.

In an exemplary system, a fluid supply 90 including a coolant, cryogenic refrigerant, or the like (in a liquid and/or a gas state), an exhaust or scavenging system (not shown) for recovering or venting expended fluid for re-use or disposal, as well as various control mechanisms for the medical system may be housed in the console 12. In addition to providing an exhaust function for the catheter fluid supply, the console 12 may also include pumps, valves, controllers or the like to recover and/or re-circulate fluid delivered to the handle 36, the catheter shaft 26, and distal end 34 of the medical device 14. A vacuum pump in the console 12 may create a low-pressure environment in one or more conduits within the medical device 14 so that fluid is drawn into the conduit(s) of the shaft 26, away from the distal end or cryogenic tip 38 and towards the proximal end of the shaft 26. The console 12 may include one or more controllers, processors, and/or software modules containing instructions or algorithms to provide for the automated operation and performance of the features, sequences, or procedures described herein.

Figure 5:
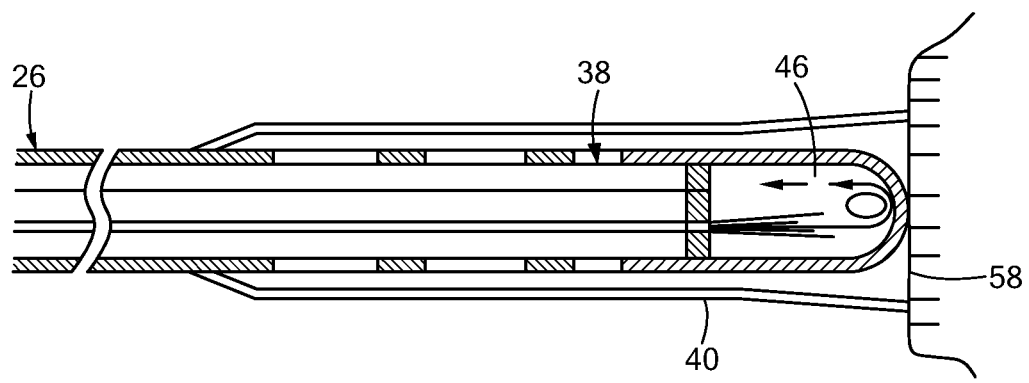
FIG. 5 is an illustration of an exemplary use of a medical device in accordance with the principles of the present invention.
Figure 6:
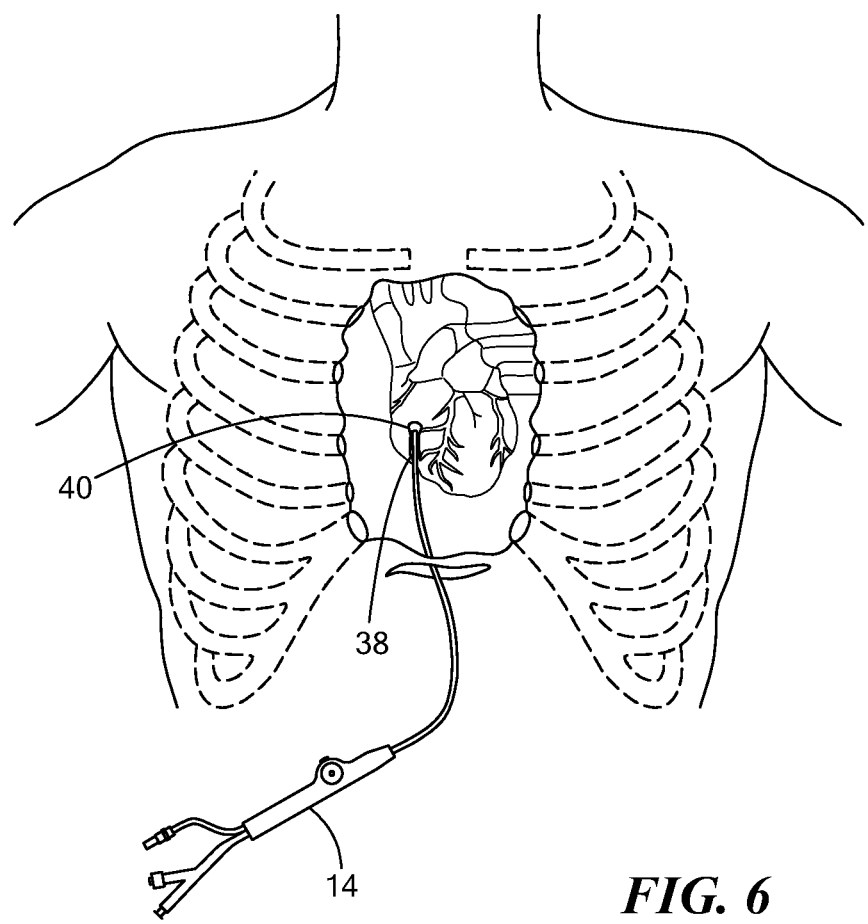
FIG. 6 is an additional illustration of an exemplary use of a medical device in accordance with the principles of the present invention.

Now referring to FIG. 5, an exemplary use of the system 10 is shown. In particular, the distal end 34 of the medical device 14 may be positioned in proximity to or otherwise adjacent to a target tissue region 58 to be treated. The introduction and positioning of the medical device 14 within the patient may include a percutaneous approach from the femoral artery or other passageway and into a desired chamber of the heart. Alternatively, the medical device may be introduced and positioned within the patient through a sub-zyphoid incision or one or more small thoracotomy incisions, as shown in FIG. 6. The introduction and positioning can be guided by use of visualization, imaging and dissection techniques, including, for example, fluoroscopy imaging in an intravascular procedure and/or video thoracoscope in a minimally invasive surgical procedure. Once the medical device has been positioned in the vicinity of the tissue to be treated, the distal surface 48 of the cryogenic tip 38 may be placed in contact with the tissue region 58, which may include cardiac tissue, for example. The thermal guard 40 may be manipulated into a desired position to effectively shield or otherwise substantially insulate the cryogenic tip 38 from the surrounding, non-treatment area and associated thermal loads. The manipulation of the thermal guard 40 may include steering or deflecting at least a portion of the guard 40, inflating the guard 40 in the embodiment having an expandable element, unwrapping or otherwise unraveling one or more pleats of the guard 40, or the like. A distal portion of the thermal guard 40 may be placed into contact with the tissue 58, and substantially shield or otherwise seal the lateral surfaces of the tip 38 from blood or other surrounding bodily fluids.

Upon obtaining the desired configuration of the thermal guard 40, the distal end 34 may be used to thermally treat the targeted tissue 58. For example, refrigerant or coolant from the fluid supply/coolant source 90 may be directed to the cryogenic tip 38 through the injection lumen 28. Upon ejection from the injection lumen 28, the refrigerant (or substantial portion thereof) may undergo two primary thermodynamic changes: (i) expanding to low pressure and temperature through positive Joule-Thomson throttling, and (ii) undergoing a phase change from liquid to vapor, thereby absorbing heat of vaporization. The resultant flow of low temperature refrigerant through the device acts to absorb heat from the target tissue and thereby cool the tissue to a desired temperature. The expanded refrigerant is then directed away from the tip 38 by the exhaust lumen 30.

By shielding or insulating a substantial portion of the distal end 34 that is not being used to thermally treat the targeted tissue, the thermal exchange is efficiently focused between the targeted tissue and the portion of the medical device 14 that is providing the therapeutic treatment. The guard 40 reduces or eliminates unwanted heat transfer between the surrounding body fluids and the cryogenic tip 38, and as a result increases the efficiency of heat transfer during thermally-based treatments, which can reduce treatment duration as well as the amount of thermal media or energy needed to perform the desired treatment.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, comprising:
    an elongate shaft having a proximal end and a distal end and a fluid path therethrough;
    a thermal treatment element at the distal end and in fluid communication with the fluid path; and
    a thermal guard coupled to an entire circumference of an outer surface of the shaft and substantially surrounding the thermal treatment element, the thermal guard defining one or more pleats.

2. The medical device of claim 1, wherein the thermal treatment element includes a chamber having a lateral surface and a distal surface, and the thermal guard substantially surrounds the lateral surface.

3. The medical device of claim 1, further comprising a cryogenic fluid source in fluid communication with the fluid path.

4. The medical device of claim 1, wherein the thermal guard is removably coupled to the elongate shaft.

5. The medical device of claim 1, wherein an annular gap is defined between the thermal guard and the thermal treatment element.

6. The medical device of claim 1, wherein the thermal guard has a substantially cylindrical shape.

7. The medical device of claim 1, wherein the thermal guard is substantially impervious to fluids.

8. A cryogenic medical system, comprising:
    a catheter having a distal tip defining a chamber with a lateral surface and a distal surface;
    a cryogenic fluid supply in fluid communication with the chamber; and
    a thermal guard defining one or more pleats and being coupled to an entire circumference of an outer surface of the catheter at a position proximal of the distal tip, the thermal guard substantially surrounding the lateral surface and exposing the distal surface.

9. The medical system of claim 8, wherein the thermal guard is removably coupled to the catheter.

10. The medical system of claim 8, wherein an annular gap is defined between the thermal guard and the distal tip.

11. The medical system of claim 8, wherein the thermal guard has a substantially cylindrical shape.

12. A method of cryogenic treatment, comprising:
    positioning a distal surface of a catheter tip into contact with tissue to be treated;
    shielding lateral surfaces of the tip from contact with body fluids using a thermal guard, the thermal guard defining one or more pleats and being coupled to an entire circumference of an outer surface of the shaft;
    circulating a coolant through a chamber inside the tip; and
    ablating the tissue with the distal surface.

13. The method of claim 12, further comprising monitoring a temperature of the tip.

14. The method of claim 12, wherein the tissue includes cardiac tissue.

* * * * *